(12) United States Patent
Ohkuma et al.

(10) Patent No.: US 8,163,947 B2
(45) Date of Patent: Apr. 24, 2012

(54) CYANATION CATALYST AND METHOD FOR PRODUCING OPTICALLY ACTIVE CYANHYDRIN COMPOUND USING THE SAME

(75) Inventors: Takeshi Ohkuma, Sapporo (JP); Nobuhito Kurono, Sapporo (JP)

(73) Assignees: National University Corporation, Hokkaido University, Sapporo (JP); Mitsubishi Rayon Co., Ltd., Tokyo (JP)

( * ) Notice: Subject to any disclaimer, the term of this patent is extended or adjusted under 35 U.S.C. 154(b) by 435 days.

(21) Appl. No.: 12/527,016

(22) PCT Filed: Feb. 14, 2008

(86) PCT No.: PCT/JP2008/052913
§ 371 (c)(1), (2), (4) Date: Aug. 13, 2009

(87) PCT Pub. No.: WO2008/099965
PCT Pub. Date: Aug. 21, 2008

(65) Prior Publication Data
US 2010/0029977 A1    Feb. 4, 2010

(30) Foreign Application Priority Data
Feb. 14, 2007    (JP) .................................. 2007-032986

(51) Int. Cl.
*C07F 9/02*    (2006.01)
*C07C 253/00*    (2006.01)
(52) U.S. Cl. ......................................... 556/19; 558/351
(58) Field of Classification Search .................... 556/19; 558/351
See application file for complete search history.

(56) References Cited

U.S. PATENT DOCUMENTS
6,248,918 B1    6/2001    Shibasaki et al.

FOREIGN PATENT DOCUMENTS
EP    0272787 A2    6/1988
JP    2000-191677 A    7/2000
JP    2006-219457 A    8/2006

OTHER PUBLICATIONS

Holmes et al., Chemically Catalyzed Asymmetric Cyanohydrin Syntheses, Angew. Chem. Int. Ed., vol. 43, May 15, 2004, pp. 2752-2778.

*Primary Examiner* — Porfirio Nazario Gonzalez
(74) *Attorney, Agent, or Firm* — McDermott Will & Emery LLP

(57) ABSTRACT

The present invention can provide a cyanation catalyst represented by the general formula (I):

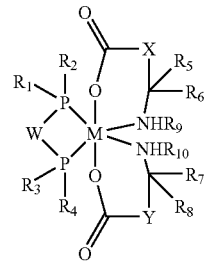

General formula (I)

(in the formula (I), $R_1$ through $R_4$ are each an optionally substituted hydrocarbon group; $R_1$ and $R_2$ and/or $R_3$ and $R_4$ may form an optionally substituted carbon chain ring; $R_5$ through $R_8$ are each a hydrogen atom, or an optionally substituted hydrocarbon group; $R_5$ and $R_6$ and/or $R_7$ and $R_8$ may form an optionally substituted carbon chain ring; $R_9$ and $R_{10}$ are each a hydrogen atom, or an optionally substituted hydrocarbon group; W, X and Y each represent an optionally substituted binding chain; X and/or Y may be non-existent; M represents a metal or a metal ion; and ligands of M may each be located at any position).

15 Claims, No Drawings

CYANATION CATALYST AND METHOD FOR PRODUCING OPTICALLY ACTIVE CYANHYDRIN COMPOUND USING THE SAME

This application is the U.S. national phase application under 35 U.S.C. §371 of International Patent Application No. PCT/JP2008/052913 filed Feb. 14, 2008, which claims the benefit of priority to Japanese Patent Application No. 2007-032986 filed Feb. 14, 2007, the disclosures of all of which are hereby incorporated by reference in their entireties. The International Application was published in Japanese on Aug. 21, 2008 as WO 2008/099965.

FIELD OF THE INVENTION

The present invention relates to a cyanation catalyst and a method for producing an optically active cyanohydrin compound using the same.

BACKGROUND OF THE INVENTION

Cyanohydrins are key intermediates for synthesizing useful substances such as optically active α-hydroxycarboxylic acids, α-hydroxyaldehydes, β-aminoalcohols and the like. One typical method for synthesizing a cyanohydrin is asymmetric cyanation reaction of an aldehyde and a ketone. A generally used reacting agent is trimethylsilyl cyanide, which is easily available. For cyanosilylation, it has been studied to use a catalyst amount of chiral Lewis acid or Lewis base (see J. Chem. Soc. Chem. Commun., 1973, pp. 55-56, and Chem. Ber., 1973, 106, pp. 587-593), and a high enantioselectivity has been reported. Furthermore, the present inventors have already proposed using a lithium salt or the like as a catalyst for cyanosilylation (see Japanese Laid-Open Patent Publication No. 2006-219457).

However, the technologies described in J. Chem. Soc. Chem. Commun., 1973, pp. 55-56, and Chem. Ber., 1973, 106, pp. 587-593 mentioned above have problems in that a large amount of catalyst (the ratio represented by substrate/catalyst is 1 to 100) is necessary, the preparation of the catalyst is troublesome, the catalyst is unstable, an excessive amount of trialkylsilyl cyanide compound with respect to a carbonyl compound needs to be used, the post-reaction treatment is troublesome, and the like.

According to the technology described in Japanese Laid-Open Patent Publication No. 2006-219457, the catalyst is easy to prepare and is highly stable, but there is a problem that an optically active product having a high enantioselectivity cannot be obtained. Namely, this technology uses only an achiral salt such as LiCl or the like as the catalyst, and so the product is entirely racemic (i.e., 0% ee).

DETAILED DESCRIPTION

The present invention has an object of providing a cyanation catalyst which is easily prepared, is highly stable, and allows an optically active cyanohydrin to be obtained; and a method for producing an optically active cyanohydrin using the same.

As a result of active studies on catalysts for allowing optically active cyanohydrins to be obtained, the present inventors found that an optically active product can be obtained by using, as a catalyst, an optically active complex (first catalyst) in addition to an achiral salt (second catalyst), which causes an asymmetric reaction.

One embodiment of the present invention is directed to a cyanation catalyst represented by the general formula (I):

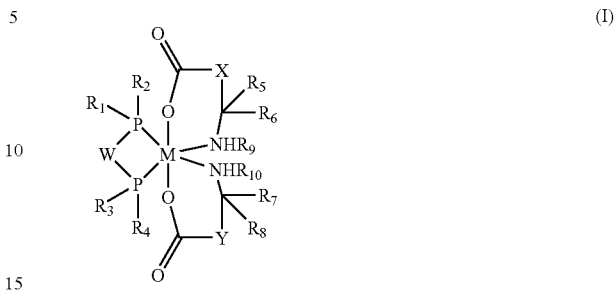

(I)

In formula (I), $R_1$ through $R_4$ may be the same as, or different from, one another, and are each an optionally substituted hydrocarbon group; $R_1$ and $R_2$ and/or $R_3$ and $R_4$ may form an optionally substituted carbon chain ring; $R_5$ through $R_8$ may be the same as, or different from, one another, and are each a hydrogen atom, or an optionally substituted hydrocarbon group; $R_5$ and $R_6$ and/or $R_7$ and $R_8$ may form an optionally substituted carbon chain ring; $R_9$ and $R_{10}$ may be the same as, or different from, each other, and are each a hydrogen atom, or an optionally substituted hydrocarbon group; W, X, and Y are same as, or different from, one another, and each represent an optionally substituted binding chain; X and/or Y may be non-existent; M represents a metal or a metal ion; and ligands of M may each be located at any position.

A preferable embodiment of the present invention is directed to a cyanation catalyst in which M in the general formula (I) is bivalent ruthenium.

Another preferable embodiment of the present invention is directed to a cyanation catalyst in which W in the general formula (I) is a 1,1'-binaphtyl group or a 1,1'-biphenyl group.

Still another preferable embodiment of the present invention is directed to a cyanation catalyst obtainable by reacting any of the above-described cyanation catalysts and a salt of a metal compound.

Yet another preferable embodiment of the present invention is directed to a cyanation catalyst in which the salt of the metal compound is at least one salt selected from the group consisting of lithium, sodium, potassium, cesium, magnesium, and lanthanoid, and/or an ammonium salt.

Another embodiment of the present invention is directed to a method for producing a cyanation catalyst represented by the general formula (I), the method comprising the steps of:

reacting a diphosphine represented by the following general formula (A) with a metal complex represented by M in the general formula (I):

(A)

In formula (A), $R_1$ through $R_4$ and W are the same as those in the formula (I), and;

reacting a reaction product obtained by the above step with an amino acid salt represented by the following general formula (B) and/or the following general formula (C):

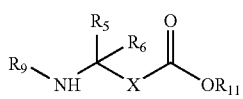
(B)

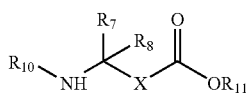
(C)

In formulas (B) and (C), X and $R_5$ through $R_{10}$ are the same as those in the formula (I); and $R_{11}$ represents a hydrogen atom or a metal compound.

A preferable embodiment of the present invention is directed to a method for producing a cyanation catalyst which further comprises the step of reacting a salt of a metal compound.

Still another embodiment of the present invention is directed to a method for producing an optically active cyanohydrin represented by the following general formula (F):

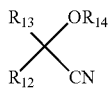
(F)

In formula (F), $R_{12}$ represents an aromatic group, a hetero ring, a chain-like alkyl group, a cyclic alkyl group, an alkenyl group or an alkynyl group, each of which may have a substituent; $R_{13}$ represents a hydrogen atom; or an alkyl group or an aromatic group, each of which may have a substituent; $R_{12}$ and $R_{13}$ may be bonded to each other to form a ring; and $R_{14}$ represents a hydrogen atom, an alkali metal, an optionally substituted hydrocarbon group, or an optionally substituted silyl group, the method comprising the steps of:

reacting, in the presence of a cyanation catalyst which is not reacted with any of the above-mentioned salts of the metal compounds, a carbonyl compound represented by the following general formula (D):

$R_{12}R_{13}C\!=\!O$ (D)

In formula (D), $R_{12}$ represents an aromatic group, a hetero ring, a chain-like alkyl group, a cyclic alkyl group, an alkenyl group or an alkynyl group, each of which may have a substituent; $R_{13}$ represents a hydrogen atom; or an alkyl group or an aromatic group, each of which may have a substituent; and $R_{12}$ and $R_{13}$ may be bonded to each other to form a ring,
with a cyanide compound represented by the general formula (E):

$R_{14}CN$ (E)

In formula (E), $R_{14}$ represents a hydrogen atom, an alkali metal, an optionally substituted hydrocarbon group, or an optionally substituted silyl group; and adding a salt of a metal compound to a reaction product obtained by the above step to cause a reaction.

Still another embodiment of the present invention is directed to a method for producing an optically active cyanohydrin represented by the following general formula (F):

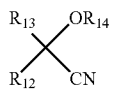
(F)

In formula (F), $R_{12}$ represents an aromatic group, a hetero ring, a chain-like alkyl group, a cyclic alkyl group, an alkenyl group or an alkynyl group, each of which may have a substituent; $R_{13}$ represents a hydrogen atom; or an alkyl group or an aromatic group, each of which may have a substituent; $R_{12}$ and $R_{13}$ may be bonded to each other to form a ring; and $R_{14}$ represents a hydrogen atom, an optionally substituted hydrocarbon group, or an optionally substituted silyl group, the method comprising the step of:

reacting, in the presence of a cyanation catalyst obtained by reacting with any one of the above-mentioned salts of the metal compounds, a carbonyl compound represented by the following general formula (D):

$R_{12}R_{13}C\!=\!O$ (D)

In the formula (D), $R_{12}$ represents an aromatic group, a hetero ring, a chain-like alkyl group, a cyclic alkyl group, an alkenyl group or an alkynyl group, each of which may have a substituent; $R_{13}$ represents a hydrogen atom; or an alkyl group or an aromatic group, each of which may have a substituent; and $R_{12}$ and $R_{13}$ may be bonded to each other to form a ring,
with a cyanide compound represented by the general formula (E):

$R_{14}CN$ (E)

In the formula (E), $R_{14}$ represents a hydrogen atom, an alkali metal, an optionally substituted hydrocarbon group, or an optionally substituted silyl group.

A preferable embodiment of the present invention is directed to a method for producing a cyanohydrin represented by the general formula (F) in which $R_{14}$ is a hydrogen atom.

Another preferable embodiment of the present invention is directed to a method for producing a cyanohydrin represented by the general formula (F) in which $R_{14}$ is trimethylsilyl (TMS).

Still another preferable embodiment of the present invention is directed to a method for producing a cyanohydrin represented by the general formula (F), characterized in that an acid anhydride is co-existent.

According to a preferable embodiment of the present invention, an optically active cyanohydrin, a catalyst for which is easy to prepare and is highly stable, is obtained.

Hereinafter, the present invention will be described in detail.

One embodiment of the present invention is directed to a cyanation catalyst represented by the general formula (I). Another embodiment of the present invention is directed to a cyanation catalyst obtained by reacting the cyanation catalyst represented by the general formula (I) used as a first catalyst, with a salt of a metal compound used as a second catalyst. These cyanation catalysts are preferably usable for producing an optically active cyanohydrin. Hereinafter, the first catalyst and the second catalyst will be described sequentially, and then a method for producing an optically active cyanohydrin using the same will be described.

First Catalyst

The first catalyst is represented by the general formula (I):

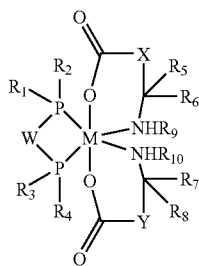

(I)

In formula (I), $R_1$ through $R_4$ may be the same as, or different from, one another, and are each an optionally substituted hydrocarbon group. $R_1$ and $R_2$ and/or $R_3$ and $R_4$ may form an optionally substituted carbon chain ring.

Specific examples of $R_1$ through $R_4$ include hydrocarbon groups such as alkyl, alkenyl, cycloalkyl, cycloalkenyl, aryl, phenylalkyl and the like. Especially, a phenyl group and a tolyl group are preferable as $R_1$ through $R_4$. Specific examples of the substituent which may be contained in $R_1$ through $R_4$ include hydrogen atom, alkyl, alkenyl, cycloalkyl, aryl, alkoxy, ester, acyloxy, halogen atom, nitro, cyano group and the like. These groups may have any of various acceptable substituents. Especially, hydrogen atom and p-methyl group are preferable as the substituent.

In the case where $R_1$ and $R_2$ (or $R_3$ and $R_4$) form a carbon chain ring, the carbon chain may have thereon any of various acceptable substituents such as alkyl, alkenyl, aryl, cycloalkyl, alkoxy, ester, acyloxy, halogen atom, nitro, cyano group and the like. As $R_1$ through $R_4$, phenyl, p-tolyl, m-tolyl, 3,5-xylyl, p-tert-butylphenyl, p-methoxyphenyl, cyclopentyl, and cyclohexyl are preferable.

$R_5$ through $R_8$ may be the same as, or different from, one another, and are each a hydrogen atom, or an optionally substituted hydrocarbon group. $R_5$ and $R_6$ and/or $R_7$ and $R_8$ may form an optionally substituted carbon chain ring.

Preferable specific examples of $R_5$ through $R_8$ include hydrogen atom, alkyl, alkenyl, alkynyl, cycloalkyl, cycloalkenyl, and aryl. Especially, it is preferable that $R_5$ and $R_7$ are hydrogen atoms and $R_6$ and $R_8$ are phenyl groups.

Specific examples of the substituent which may be contained in $R_5$ through $R_8$ include various acceptable substituents such as alkyl, alkenyl, cycloalkyl, aryl, alkoxy, ester, acyloxy, halogen atom, nitro, cyano group and the like. Especially, hydrogen atom, methyl group and methoxy group are preferable as the substituent.

In the case where $R_5$ and $R_6$ (or $R_7$ and $R_8$) form a carbon chain ring, the carbon chain may have thereon any of various acceptable substituents such as alkyl, alkenyl, aryl, cycloalkyl, alkoxy, ester, acyloxy, halogen atom, nitro, cyano group and the like. It is preferable that $R_5$ and $R_7$ are hydrogen atoms and $R_6$ and $R_8$ are phenyl groups as $R_5$ through $R_8$.

$R_9$ and $R_{10}$ may be the same as, or different from, each other, and are each a hydrogen atom, or an optionally substituted hydrocarbon group.

Specific examples of $R_9$ and $R_{10}$ include hydrogen atom and hydrocarbon groups such as alkyl, alkenyl, cycloalkyl, cycloalkenyl, aryl, phenylalkyl and the like. Especially, hydrogen atom is preferable as $R_9$ and $R_{10}$. Specific examples of the substituent which may be contained in $R_9$ and $R_{10}$ include various acceptable substituents such as alkyl, alkenyl, cycloalkyl, aryl, alkoxy, ester, acyloxy, halogen atom, nitro, cyano group and the like. Especially, hydrogen atom, methyl group and methoxy group are preferable as the substituent.

Examples of the binding chain represented by W in the general formula (I) include bivalent hydrocarbon chains (for example, straight-chain hydrocarbons such as $-CH_2-$, $-(CH_2)_2-$, $-(CH_2)_3-$, $-(CH_2)_4-$, and the like; branched hydrocarbon chains such as $-CH_2CH(CH_3)-$, $-CH(CH_3)CH(CH_3)-$, and the like; cyclic hydrocarbon chains such as $-C_6H_4-$, $-C_6H_{10}-$, and the like; etc.) bivalent binaphtyl, bivalent biphenyl, bivalent paracyclophane, bivalent bipyridine, bivalent cyclic heterocycle, and the like. Among these, 1,1'-binaphtyl group or 1,1'-biphenyl group, which may have a substituent and in which position 2 or position 2' is bonded to phosphine, are preferable. These binding chains may have any of various acceptable substituents such as alkyl, alkenyl, cycloalkyl, aryl, alkoxy, ester, acyloxy, halogen atom, nitro, cyano group and the like. The substituents may be bonded to each other via a carbon atom, an oxygen atom, a nitrogen atom, a sulfur atom or the like. W preferably has an optical activity. For example, in the case where W contains a 1,1'-binaphtyl group, the 1,1'-binaphtyl group is preferably an (R)-1,1'-binaphtyl group or an (S)-1,1'-binaphtyl group. In the case where W contains a 1,1'-biphenyl group, the 1,1'-biphenyl group is preferably an (R)-1,1'-biphenyl group or an (S)-1,1'-biphenyl group.

A diphosphine derivative ($R_1R_2P-W-PR_3R_4$), which is a bidentate ligand containing W, coordinates at M. Thus, the diphosphine derivative is a preferable specific example of W. Examples of the diphosphine derivative include BINAP (2,2'-bis(diphenylphosphino)-1,1'-binaphtyl), TolBINAP (2,2'-bis[(4-methylphenyl)phosphino]-1,1'-binaphtyl), Xy 1 BINAP (2,2'-bis[(3,5-dimethylphenyl)phosphino]-1,1'-binaphtyl), 2,2'-bis[(4-t-butylphenyl)phosphino]-1,1'-binaphtyl, 2,2'-bis[(4-isopropylphenyl)phosphino]-1,1'-binaphtyl, 2,2'-bis[(naphthalene-1-yl)phosphino]-1,1'-binaphtyl, 2,2'-bis[(naphthalene-2-yl)phosphino]-1,1'-binaphtyl, BICHEMP (2,2'-bis(dicyclohexylphosphino)-6,6'-dimethyl-1,1'-biphenyl), BPPFA (1-[1,2-bis-(diphenylphosphino)ferrocenyl]ethylamine), CHIRAPHOS (2,3-bis(diphenylphosphino)butane), CYCPHOS (1-cyclohexyl-1,2-bis(diphenylphosphino)ethane), DEGPHOS (1-substituted-3,4-bis(diphenylphosphino)pyrrolidine), DIOP (2,3-isopropylidene-2,3-dihydroxy-1,4-bis(diphenylphosphino)butane), SKEWPHOS (2,4-bis(diphenylphosphino)pentane), DuPHOS (substituted-1,2-bis(phospholano)benzene), DIPAMP (1,2-bis[(o-methoxyphenyl)phenylphosphino]ethane), NORPHOS (5,6-bis(diphenylphosphino)-2-norbornene), PROPHOS (1,2-bis(diphenylphosphino)propane), PHANEPHOS (4,12-bis(diphenylphosphino)-[2,2']-paracyclophane), substituted-2,2'-bis(diphenylphosphino)-1,1'-bipyridine, SEGPHOS ((4,4'-bi-1,3-benzodioxol)-5,5'-diyl-bis(diphenylphosphino)), BIFAP (2,2'-bis(diphenylphosphanyl)-1,1'-bidibenzofuranyl), and the like.

Especially, BINAP (2,2'-bis(diphenylphosphino)-1,1'-binaphtyl) and TolBINAP (2,2'-bis[(4-methylphenyl)phosphino]-1,1'-binaphtyl) are preferable as the diphosphine derivative.

In the general formula (I), X and Y may be same as, or different from, each other, and are each a binding chain which may have a substituent. X and/or Y may be non-existent.

Specific examples of X and Y include bivalent hydrocarbon chains (for example, straight-chain hydrocarbons such as $-CH_2-$, $-(CH_2)_2-$, $-(CH_2)_3-$, $-(CH_2)_4-$, and the like; branched hydrocarbon chains such as $-CH_2CH(CH_3)-$, $-CH(CH_3)CH(CH_3)-$, and the like; cyclic hydrocarbon chains such as $-C_6H_4-$, $-C_6H_{10}-$, and the like; etc.), bivalent cyclic heterocycle, and the like.

A case where X and/or Y are non-existent is, for example, a case where $C=$ and $C(R_5)R_6$ are directly bonded to each other as in a compound represented by the following formula (II).

In the general formula (I), M represents a metal or a metal ion. Specific examples of M include Ru, Fe, Pd, Rh, Co, and the like. Especially, bivalent ruthenium is preferable as M.

In the general formula (I), the recitation that each ligand of M may be located at any position means that the positions of N, P, O, and O bonded to M are arbitrary. For example, in the general formula (I), O and O face each other while interposing M therebetween, but, for example, O and N, and O and P, may face each other.

A specific example of the first catalyst is a compound represented by the general formula (II) (Ru[(S)-phenylglycine]$_2$[(S)-binap]).

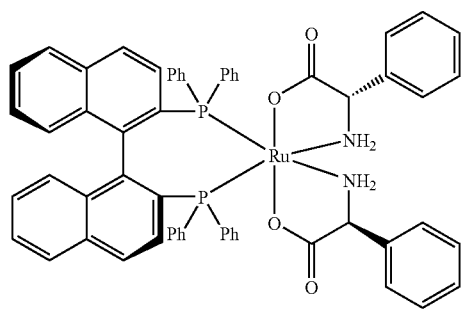

(II)

(Production of the First Catalyst)

A method for producing the first catalyst includes the step of reacting a diphosphine represented by the following general formula (A) with a metal complex represented by M in the general formula (I):

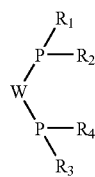

(A)

In formula (A), $R_1$ through $R_4$ and W are the same as those in the formula (I); and the step of reacting a reaction product obtained by the above step with an amino acid salt represented by the following general formula (B) and/or the general formula (C):

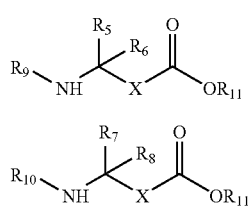

(B)

(C)

In formulas (B) and (C), X and $R_5$ through $R_{10}$ are the same as those in the formula (I); and $R_{11}$ represents a hydrogen atom or a metal compound.

Preferable examples of each substituent in the general formulas (A) through (C) are the same as those listed above as preferable examples of the substituents in the description regarding the general formula (I).

One exemplary method for producing the first catalyst is as follows. First, a complex of M (bivalent chloride complex of ruthenium, etc.) and optically active diphosphine represented by the general formula (A) are reacted with each other to produce a diphosphine complex solution of M. Next, a solution (usually an alcohol solution such as methanol or the like) of optically active amino acid salt (for example, sodium salt) represented by the general formula (B) or (C) is added to the diphosphine complex solution to form a complex, and the complex is isolated and purified by thin layer chromatography or the like.

The diphosphine complex solution of M can be produced in a solvent (e.g., an organic solvent such as DMF solvent or the like) by stirring under heating (e.g., stirring at 80 to 120° C. (preferably, about 100° C.) for 5 to 20 minutes (preferably, about 10 minutes)). The conditions under which the solution of optically active amino acid salt represented by the general formula (B) or (C) is added to the diphosphine complex solution of M to cause a reaction may be, for example, stirring at 10 to 30° C. (preferably, around room temperature) for 8 to 15 hours (preferably, about 12 hours).

Second Catalyst

The second catalyst is a salt of a metal compound, and is preferably selected from at least one salt selected from the group consisting of lithium, sodium, potassium, cesium, magnesium, and lanthanoid, and/or an ammonium salt. The second catalyst is a cocatalyst of the first catalyst.

Examples of the salt of lithium include lithium halides (LiF, LiCl, LiBr, LiI), LiClO$_4$, Li(OTf), Li(OAc), LiCN, Li$_2$CO$_3$, and the like, and other salts may also be used. The lithium salts described in Japanese Laid-Open Patent Publication No. 2006-219457 (see paragraph [0008]) may also be used. LiCl and/or LiClO$_4$ are especially preferable.

As the salts of sodium, potassium, and cesium, any of salts corresponding to the above-mentioned lithium salts may be used. An example of the salt of magnesium is magnesium triflate. An example of the salt of lanthanoid is ytterbium triflate. Examples of the salt of ammonium include organic ammonium salts such as tetrabutylammonium chloride and the like.

The cyanation catalyst as one embodiment of the present invention uses, as a catalyst, an optically active complex (first catalyst) in addition to an achiral salt (second catalyst), and therefore allows an optically active product to be obtained. By contrast, in the case where only an achiral salt such as LiCl or the like is used as the catalyst (for example, the catalysts described in Japanese Laid-Open Patent Publication No. 2006-219457), the product is entirely racemic (i.e., 0% ee).

Namely, where only an achiral salt such as LiCl or the like is used as the catalyst, an achiral reaction occurs. In contrast, according to the present invention, an asymmetric reaction can occur.

Method for Producing an Optically Active Cyanohydrin

Another embodiment of the present invention is directed to a method for producing an optically active cyanohydrin represented by the following general formula (F), which includes the step of reacting a carbonyl compound represented by $R_{12}R_{13}C=O$ (general formula (D)) with a cyanide compound represented by $R_{14}CN$ (general formula (E)) in the presence of the first catalyst; and the step of adding the second catalyst to the reaction product obtained by the above step to cause a reaction.

Still another embodiment of the present invention is directed to a method for producing an optically active cyanohydrin represented by the following general formula (F), which includes the step of reacting a carbonyl compound represented by the general formula (D) with a cyanide compound represented by the general formula (E) in the presence of a catalyst obtained by reacting the first catalyst with the second catalyst.

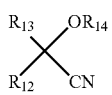
(F)

In formula (F), $R_{12}$ represents an aromatic group, a hetero ring, a chain-like alkyl group, a cyclic alkyl group, an alkenyl group or an alkynyl group, each of which may have a substituent. $R_{13}$ represents a hydrogen atom; or an alkyl group or an aromatic group, each of which may have a substituent. $R_{12}$ and $R_{13}$ may be bonded to each other to form a ring. $R_{14}$ represents a hydrogen atom, an optionally substituted hydrocarbon group, or an optionally substituted silyl group.

Examples of the aromatic group which may be represented by $R_{12}$ include phenyl, tolyl, xylyl, naphtyl, and the like. These aromatic groups may have any of various acceptable substituents such as alkyl, alkenyl, cycloalkyl, aryl, alkoxy, ester, acyloxy, halogen atom, nitro, cyano, and the like.

Examples of the hetero ring which may be represented by $R_{12}$ include those having a five-membered ring structure such as pyrrole, thiophene, furan, pyrazole, imidazole, thiazole, oxazole, and the like; and those having a six-membered ring structure such as pyridine, pyrimidine, pyridazine, and the like. These hetero rings may have any of various acceptable substituents such as alkyl, alkenyl, cycloalkyl, aryl, alkoxy, ester, acyloxy, halogen atom, nitro, cyano, and the like.

Examples of the chain-like alkyl group which may be represented by $R_{12}$ include those with no branch such as methyl, ethyl, propyl, n-butyl, and the like; and those with a branch such as isopropyl, sec-butyl, and the like.

Examples of the cyclic alkyl group which may be represented by $R_{12}$ include cyclopentyl, cyclohexyl, and the like. These cyclic alkyl group may have a substituent usable for the above-described aromatic groups, such as alkyl or the like.

Examples of the alkenyl group which may be represented by $R_{12}$ include ethenyl group, propenyl group, butenyl group, propenyl group, and the like.

Examples of the alkynyl group which may be represented by $R_{12}$ include ethynyl group, propynyl group, butynyl group, and the like.

Examples of the alkyl group which may be represented by $R_{13}$ include methyl, ethyl, propyl, isopropyl, butyl, isobutyl, sec-butyl, tert-butyl, and the like. These alkyl groups may have any of various acceptable substituents such as aryl, cycloalkyl, alkoxy, ester, acyloxy, halogen atom, nitro, cyano, and the like.

Examples of the aromatic group which may be represented by $R_{13}$ include phenyl, tolyl, xylyl, naphtyl, and the like. These aromatic groups may have any of various acceptable substituents such as alkyl, alkenyl, cycloalkyl, aryl, alkoxy, ester, acyloxy, halogen atom, nitro, cyano, and the like.

An example of the ring formed by $R_{12}$ and $R_{13}$ bonded to each other is a carbon chain. This carbon chain may have thereon any of various acceptable substituents such as alkyl, alkenyl, cycloalkyl, aryl, alkoxy, ester, acyloxy, halogen atom, nitro, cyano, and the like.

Examples of the hydrocarbon group which may be represented by $R_{14}$ include aliphatic or alicyclic saturated or unsaturated hydrocarbon groups, single-ring aromatic or aromatic-aliphatic hydrocarbon, multi-ring aromatic or aromatic-aliphatic hydrocarbon, and the like. These hydrocarbon groups may have any of various acceptable substituents such as alkyl, alkenyl, cycloalkyl, aryl, alkoxy, ester, acyloxy, halogen atom, nitro, cyano, and the like. The silyl groups which may be represented by $R_{14}$ may have any of various acceptable substituents such as alkyl, alkenyl, cycloalkyl, aryl, alkoxy, ester, acyloxy, halogen atom, nitro, cyano, and the like.

Specific examples of the hydrocarbon group include alkyl, alkenyl, cycloalkyl, cycloalkenyl, phenyl, tolyl, xylyl, naphtyl, phenylalkyl, and the like.

Specific examples of the silyl group include trimethylsilyl, di-t-butylmethylsilyl, diphenyl-t-butylsilyl, and the like.

As the carbonyl compound, which is a substrate, $R_{12}R_{13}C=O$ (in the formula, $R_{12}$ and $R_{13}$ represent the same as those in the formula (F)) may be used.

Typical examples of the carbonyl compound, which is a substrate, include benzaldehyde and derivatives thereof (having a substituent such as alkyl, alkoxy, trifluoromethyl, halogen, or the like on the benzene ring), acetophenone and derivatives thereof (having halogen, trifluoromethyl, cyano, nitro, or alkoxy on the benzene ring), and the like.

As the cyanide compound, $R_{14}CN$ (in the formula, $R_{14}$ represents the same as those in the formula (F)) may be used.

As the cyanide compound ($R_{14}CN$), which is an original material, NaCN, KCN, or the like may be used. Therefore, in this case, $R_{14}$ may be an alkali metal such as Na, K, or the like.

The molar ratio of the carbonyl compound with respect to the cyanation catalyst according to the present invention, i.e., S/C (S is the carbonyl compound as the substrate; and C is the catalyst) is preferably 1 to 1000000, and more preferably 1 to 100000. The molar ratio of the cyanide compound with respect to the carbonyl compound is preferably 1 to 3, and more preferably 1 to 1.3.

The cyanation catalyst according to the present invention is especially useful for cyanation of a carbonyl compound having a hetero atom at position α of carbonyl carbon. Examples of such a carbonyl compound include, but not specifically limited to, α-chloroacetophenone, α-methoxyacetophenone, α,α-diethoxyacetophenone, α,α-dimethoxyacetone, and the like.

The cyanation reaction for producing cyanohydrin is preferably performed in an atmosphere of inert gas such as argon or the like at normal pressures.

The cyanation reaction proceeds without a solvent or in a reaction solvent. Examples of the reaction solvent include aromatic hydrocarbon solvents such as toluene, xylene, and the like; aliphatic hydrocarbon solvents such as pentane, hexane, and the like; halogen-containing hydrocarbon solvents such as methylene chloride and the like; ether-based solvents such as ether, tetrahydrofran (THF), and the like; and hetero atom-containing solvents such as acetonitrile, N,N-dimethylacetoamide (DMA), N,N-dimethylformamide (DMF), N-methylpyrrolidone, dimethylsulfoxide (DMSO), and the like. For dissolving the cyanation catalyst according to the present invention to be used for the reaction, the same solvents as those mentioned above may be used.

The reaction temperature is not specifically limited, but is preferably −78 to 50° C., and more preferably 0 to 30° C. The reaction time varies in accordance with the type of the substrate or the like, but is in the range of 1 minute to 12 hours in many cases. For sampling cyanohydrin from the reaction mixture solution after the reaction is finished, distillation or extraction may be used.

By reacting a carbonyl compound with a cyanide compound in the presence of the above-described cyanation catalyst, corresponding cyanohydrin can be produced. Specifically, for example, a catalyst solution obtained by dissolving the cyanation catalyst in an organic solvent, or a solidified cyanation catalyst (solidified catalyst), is put into a container accommodating a carbonyl compound (an aldehyde or a ketone) and a cyanide compound, and the substances are stirred. As a result, the carbonyl compound and the cyanide compound can be reacted with each other.

In the case where the carbonyl compound is oily, the catalyst solution or the solidified catalyst may be put into a solvent-free container accommodating the carbonyl compound and the cyanide compound to cause a reaction. In the case where the carbonyl compound is solid, the catalyst solution or the solidified catalyst may be put into a container accommodating the carbonyl compound, the cyanide compound and a reaction solvent to cause a reaction.

EXAMPLES

Hereinafter, the present invention will be described in details by way of examples, which do not limit the present invention in any way.

Example 1

Production of First Catalyst

In a 100 ml Schlenk flask A fully heated and dried, benzene ruthenium chloride dimer (375 mg, 0.75 mmol) and (S)-BINAP (2,2-bis(diphenylphosphino)-1,1'-bisnaphtyl) (935 mg, 1.50 mmol) were dissolved in DMF (15 ml, dehydrating solvent produced by Kanto Chemical Co., Inc., treated with lyophilizing deaeration (3 cycles)) in an argon atmosphere. The resultant substance was stirred for 10 minutes while being heated in an oil bath of 100° C. to be converted into $RuCl_2[(S)\text{-binap}](dmf)_n$ (this intermediate is a known compound, and is synthesized in, for example, Org. Synth., 1993 (see pages 72 and 74). This was left to be cooled down to room temperature (20 to 25° C.).

(S)-phenylglycine (519 mg, 3 mmol) dissolved in methanol (30 ml, dehydrating solvent produced by Kanto Chemical Co., Inc.) was added to a 50 ml Schlenk flask B, treated with lyophilizing deaeration (3 cycles), and then returned to room temperature.

Next, in an argon atmosphere, the above-mentioned phenylglycine solution was added, while being stirred, to the Schlenk flask A in which $RuCl_2[(S)\text{-binap}](dmf)_n$ was prepared. Immediately, the reddish brown color changed to a yellowish orange color. This substance was stirred at the same temperature for 12 hours. While this substance was stirred, distilled water (50 mL) was added thereto. Then, a yellowish orange solid was dispersed in the aqueous solution. The solid content in the solution was taken out by filtration, dissolved in methylene chloride (50 ml), and then washed with distilled water (50 ml) 5 times. The methylene chloride phase was dried with sodium sulfate or magnesium sulfate and filtered by a Celite pad, and the solvent was removed at a reduced pressure. Thus, a yellow to yellowish orange solid was obtained.

This solid was isolated and purified by thin layer chromatography (silica gel; developing solvent: ethyl acetate; extracting solvent: methylene chloride/methanol=10/1). The obtained solid was dissolved in a small amount of methylene chloride and dropped onto diethylether or pentane with stirring. As a result, a yellow solid was dispersed. The solid was taken out by filtration and dried at a reduced pressure. The dried substance was Ru[(S)-phenylglycine]$_2$[(S)-BINAP] (the compound of the formula (II) and (III)).

Various properties of the dried substance are shown below:
mp>203° C. (decomposition)
$^1$H NMR (400 MHz, CDCl$_3$) δ2.45 (m, 2H, NHH), 3.25 (m, 2H, NHH), 3.63 (m, 2H, CH), 6.23-8.08 (m, 42H, aromatic H). This assignment was confirmed by $^1$H-$^{13}$C COSY.
$^{31}$P NMR (161.7 MHz, CDCl$_3$) δ52.3 (s)
FAB-MS (relative intensity) 1024 (75), 874 (100), 723 (75), 647 (22).
FAB-HRMS Calcd for $C_{60}H_8N_2O_4P_2Ru$ m/z 1024.05. Found m/z 1024.21.

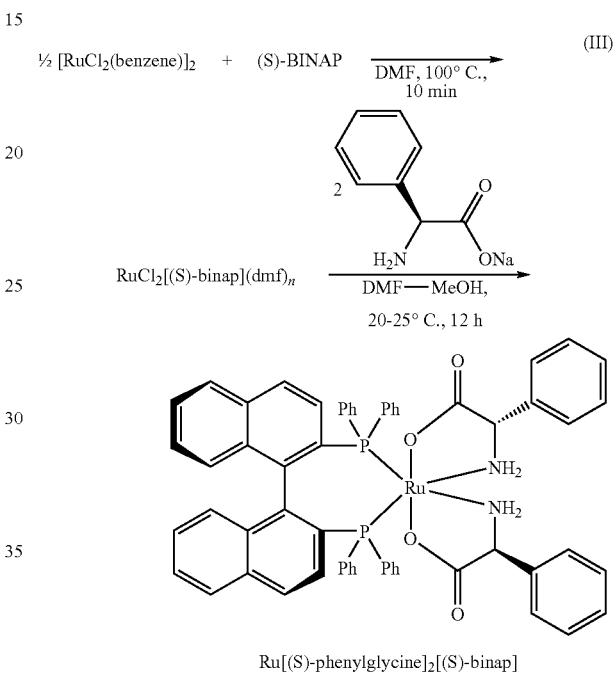

Ru[(S)-phenylglycine]$_2$[(S)-binap]

Example 2

Production of First Catalyst

A target substance of the formula (III) was obtained in exactly the same manner as in Example 1 except that racemic phenylglycine was used instead of (S)-phenylglycine. At the time of isolation and purification by thin layer chromatography, diastereomer generated at the same time by the reaction was allowed to be separated. As a result, pure Ru [(S)-phenylglycine]$_2$ [(S)-BINAP] and Ru[(R)-phenylglycine]$_2$[(S)-BINAP] were obtained. They are the same as the target substance of Example 1, and the properties were as described above.

Example 3

Asymmetric Cyanosilylation of Benzaldehyde (Preparation of the Second Catalyst (Lithium Chloride Solution))

Lithium chloride (21.2 mg, 500 μmol; produced by Aldrich; anhydride) was added to a 10 ml side arm flask, and the inside of the flask was substituted with argon. THF (10 mL, dehydrating solvent produced by Kanto Chemical Co., Inc., treated with lyophilizing deaeration (3 cycles)) was added thereto, and lithium chloride was dissolved in THF.
(Preparation of the First Catalyst (Ruthenium Complex Solution))

Ru[(S)-phenylglycine]$_2$-[(S)-binap] (compound of the formula (III), 10.2 mg, 10 μmol) was added to a 10 ml side arm flask, and the inside of the flask was substituted with argon. THF (0.5 mL, dehydrating solvent produced by Kanto Chemical Co., Inc. treated with lyophilizing deaeration (3 cycles)) was added thereto, and Ru[(S)-phenylglycine]$_2$[(S)-binap] was dissolved in THF.
(Asymmetric Cyanosilylation Reaction)

$^t$BuOMe (5 mL) and a THF solution of the first catalyst (Ru[(S)-phenylglycine]$_2$[(S)-binap]) (50 μl; 1 μmol when converted into Ru complex) were added to a 25 ml side arm flask of an argon atmosphere, and also benzaldehyde (1.01 ml, 10 mmol; produced by Kanto Chemical Co., Inc.; immediately after distilled) and trimethylsilyl cyanide (1.33 ml, 10 mmol; produced by Wako Chemical, Ltd.; within 1 week after distilled) were added thereto. The resultant substance was cooled over 10 minutes to −20° C. (the temperature of the constant temperature bath).

Into this flask, a THF solution of the second catalyst (lithium chloride) (20 μl; 1 μmol when converted into lithium chloride) was put by a microsyringe and stirred at −20° C. for 1 hour. Tetralin (1.08 ml, 8 mmol) as the internal standard was added and stirred. A sample of the reaction solution was taken out and measured by gas chromatography to calculate the yield of the generated product and the enantiomer excess (the formula (IV); yield: 100%; 83% ee).

(IV)

[Structure: benzaldehyde + (CH$_3$)$_3$SiCN → product]

Ru complex/LiCl
$^t$BuOMe, 1 h,
−20° C. (bath temp)

S/C (Ru complex) = 10000
S/C (LiCl) = 10000

[Structure: product with OSi(CH$_3$)$_3$ and CN]

100%, 83% ee (R)

Example 4

Asymmetric Cyanosilylation of 2,2-Diethoxyacetophenone (Preparation of the First and Second Catalysts)

A solution of the first catalyst (Ru[(S)-phenylglycine]$_2$ [(S)-binap]) and a solution of the second catalyst (lithium chloride) were prepared in exactly the same manner as in Example 3.
(Asymmetric Cyanosilylation Reaction)

Ru[(S)-phenylglycine]$_2$[(S)-binap] (20.5 mg, 20 μmol) was added to a 25 ml side arm flask to generate an argon atmosphere. Into this flask, $^t$BuOMe (5 mL), 2,2-diethoxyacetophenone (2.0 ml, 10 mmol; produced by Kanto Chemical Co., Inc.; immediately after distilled), and trimethylsilyl cyanide (1.33 ml, 10 mmol; produced by Wako Chemical, Ltd.; within 1 week after distilled) were added and cooled at 0° C. (the temperature of the constant temperature bath) for 10 minutes. Experiments in which the cooling temperature was −20° C. and −78° C. were also performed in substantially the same manner. To this flask, a THF solution of lithium chloride (20 μl; 1 μmol when converted into lithium chloride) was added by a microsyringe and stirred at 0° C. for 1 hour. In the experiments in which the cooling temperature was −20° C. and −78° C., the temperature at the time of stirring was −20° C. and −78° C., respectively. Tetralin (1.08 ml, 8 mmol) as the internal standard was added and stirred. A sample of the reaction solution was taken out and measured by gas chromatography to calculate the yield of the generated product and the enantiomer excess (the formula (V); 0° C.: yield: 100%; 83% ee; −20° C.: yield: 95%; 88% ee; −78° C.: yield: 100%; 94% ee).

(V)

[Structure: 2,2-diethoxyacetophenone + (CH$_3$)$_3$SiCN → product]

Ru complex
LiCl
$^t$BuOMe, 1 h

S/C (Ru complex) = 500
S/C (LiCl) = 10000

[Structure: product with NC, OSi(CH$_3$)$_3$, OC$_2$H$_5$, OC$_2$H$_5$]

0° C.: 100%, 84% ee
−20° C.: 95%, 88% ee

Example 5

Asymmetric Cyanosilylation of o-methylbenzaldehyde (Preparation of the First and Second Catalysts)

A solution of the first catalyst (Ru[(S)-phenylglycine]$_2$ [(S)-binap]) and a solution of the second catalyst (lithium chloride) were prepared in exactly the same manner as in Example 3.
(Asymmetric Cyanosilylation Reaction)

Into a 25 ml side arm flask of an argon atmosphere, a THF solution of Ru[(S)-phenylglycine]$_2$[(S)-binap] (50 μl; 1 μmol when converted into Ru complex) and $^t$BuOMe (5 mL) were added, and also o-methylbenzaldehyde (1.15 ml, 10 mmol; produced by Kanto Chemical Co., Inc.; immediately after distilled) and trimethylsilyl cyanide (1.33 ml, 10 mmol; produced by Wako Chemical, Ltd.; within 1 week after distilled) were added thereto. The resultant substance was cooled at 0° C. (the temperature of the constant temperature bath) for 10 minutes. An experiment in which the cooling temperature was −78° C. was also performed in substantially the same manner.

Into this flask, a THF solution of lithium chloride (20 μl; 1 μmol when converted into lithium chloride) was added by a microsyringe and stirred at 0° C. for 1 hour. Tetralin (1.08 ml, 8 mmol) as the internal standard was added and stirred. A sample of the reaction solution was taken out and measured by gas chromatography to calculate the yield of the generated product and the enantiomer excess (the formula (VI); 0° C.: yield: 100%; 73% ee; −78° C.: yield: 100%; 95% ee).

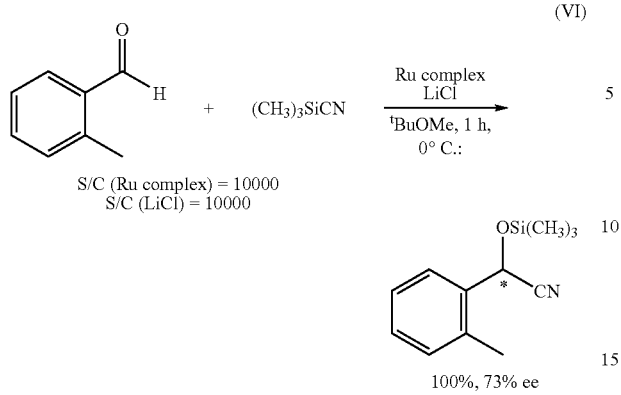

100%, 73% ee

Example 6

Asymmetric Cyanosilylation of o-chlorobenzaldehyde

An asymmetric cyanosilylation reaction was caused in exactly the same manner as in Example 5 except that instead of o-methylbenzaldehyde, the same molar amount of o-chlorobenzaldehyde was used.

A sample of the reaction solution was taken out and measured by gas chromatography to calculate the yield of the generated product and the enantiomer excess (the formula (VII); yield: 100%; 59% ee).

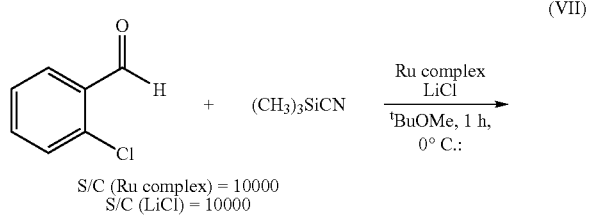

100%, 59% ee

Example 7

Asymmetric Cyanosilylation of m-anisaldehyde

An asymmetric cyanosilylation reaction was caused in exactly the same manner as in Example 5 except that instead of o-methylbenzaldehyde, the same molar amount of m-anisaldehyde was used and that the time for asymmetric cyanosilylation was extended from 1 hour to 3 hours.

A sample of the reaction solution was taken out and measured by gas chromatography to calculate the yield of the generated product and the enantiomer excess (the formula (VIII); 0° C.: yield: 100%; 76% ee; −78° C.: yield: 100%; 92% ee).

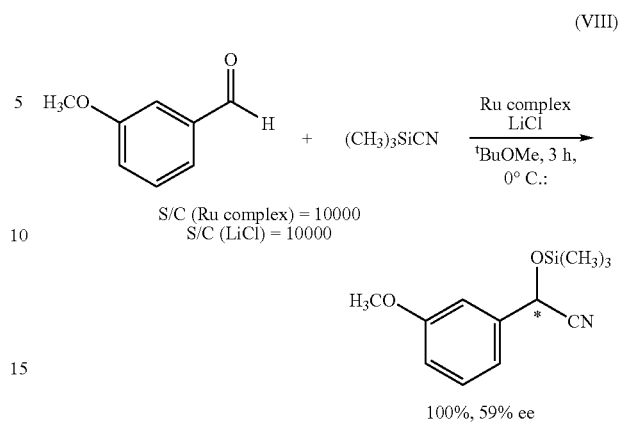

100%, 59% ee

Example 8

Asymmetric Cyanosilylation of 2-naphtylaldehyde (Preparation of the First and Second Catalysts)

A solution of the first catalyst (Ru[(S)-phenylglycine]$_2$[(S)-binap]) and a solution of the second catalyst (lithium chloride) were prepared in exactly the same manner as in Example 3.

(Asymmetric Cyanosilylation Reaction)

Ru[(S)-phenylglycine]$_2$[(S)-binap] (20.5 mg, 20 μmol) and 2-naphtoaldehyde (1.56 g, 10 mmol) were added to a 25 ml side arm flask to generate an argon atmosphere. Into this flask, $^t$BuOMe (5 mL) and trimethylsilyl cyanide (1.33 ml, 10 mmol; produced by Wako Chemical, Ltd.; within 1 week after distilled) were added.

To this flask, a THF solution of lithium chloride (20 μl; 1 μmol when converted into lithium chloride) was added by a microsyringe and stirred at room temperature (20 to 25° C.) for 1 hour. Tetralin (1.08 ml, 8 mmol) as the internal standard was added and stirred. A sample of the reaction solution was taken out and measured by gas chromatography to calculate the yield of the generated product and the enantiomer excess (the formula (IX); yield: 100%; 72% ee).

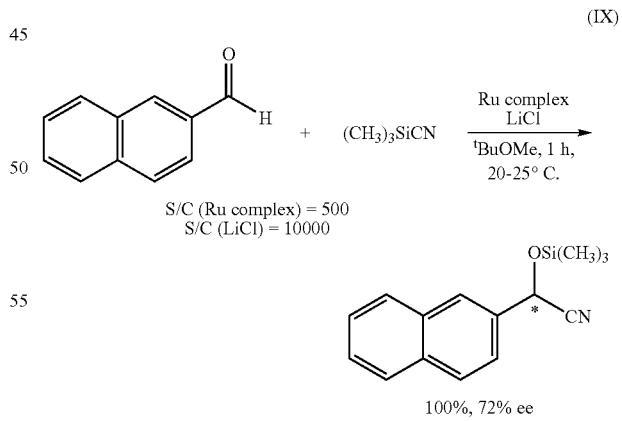

100%, 72% ee

Example 9

Asymmetric Cyanosilylation of Pivalaldehyde

An asymmetric cyanosilylation reaction was caused in exactly the same manner as in Example 8 except that instead of 2-naphtylaldehyde, the same molar amount of pivalaldehyde was used. The reaction was also caused by stirring at −78° C. for 10 hours.

A sample of the reaction solution was taken out and measured by gas chromatography to calculate the yield of the generated product and the enantiomer excess (the formula (X); room temperature: yield: 100%; 67% ee; −78° C.: yield: 100%; 94% ee).

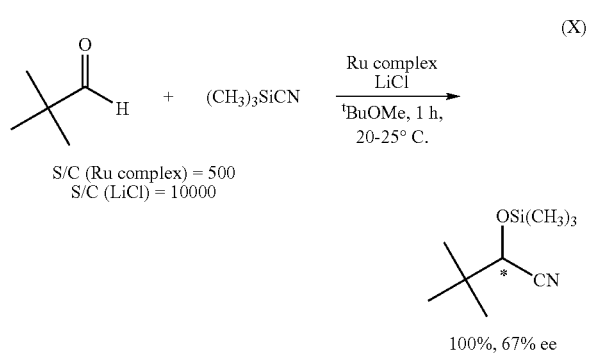

Example 10

Asymmetric Cyanosilylation of Cinnamaldehyde

An asymmetric cyanosilylation reaction was caused in exactly the same manner as in Example 8 except that instead of 2-naphtylaldehyde, the same molar amount of cinnamaldehyde was used.

A sample of the reaction solution was taken out and measured by gas chromatography to calculate the yield of the generated product and the enantiomer excess (the formula (XI); yield: 100%; 57% ee).

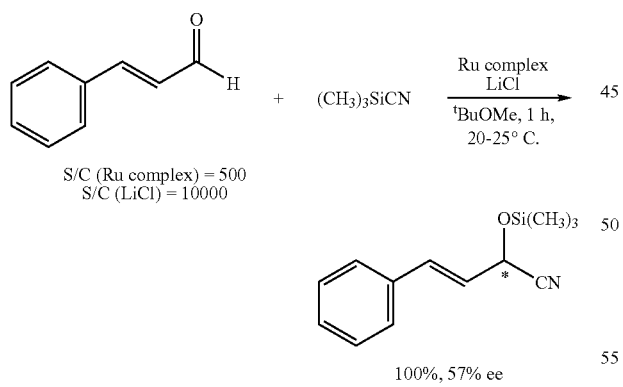

Example 11

An asymmetric cyanosilylation reaction was caused in exactly the same manner as in Example 3 except that instead of t-BuOMe, hexane was used and that the reaction temperature was 0° C. A sample of the reaction solution was taken out and measured by gas chromatography to calculate the yield of the generated product and the enantiomer excess (yield: 100%; 65% ee).

Example 12

An asymmetric cyanosilylation reaction was caused in exactly the same manner as in Example 3 except that instead of t-BuOMe, toluene was used and that the reaction temperature was 0° C. A sample of the reaction solution was taken out and measured by gas chromatography to calculate the yield of the generated product and the enantiomer excess (yield: 100%; 71% ee).

Example 13

Asymmetric Cyanation of Benzaldehyde (Preparation of Hydrogen Cyanide Solution)
Tert-butylmethylether (18 ml; hereinafter, referred to as "TBME") and trimethylsilane cyanide (0.75 ml, 6 mmol) were added to a 50 ml Schlenk flask of an argon atmosphere containing a stirrer, and cooled at 0° C. for 10 minutes. Then, 2-propanol (0.46 ml, 6 mmol) was added by a syringe and stirred at the same temperature for 15 minutes.
(Asymmetric Hydrocyanation Reaction)
The Schlenk flask containing the hydrogen cyanide solution was cooled at −40° C. for 40 minutes. Then, benzaldehyde (0.51 ml, 5 mmol), a THF solution of Ru[(S)-phenylglycine]$_2$[(S)-binap] (100 µl; corresponding to 10 µmol), and a THF solution of lithium chloride (100 µl, corresponding to 10 µmol) were added thereto to cause a reaction at −40° C. for 6 hours. After the reaction was finished, 0.1 N acetone hydrochloride solution (pre-adjusted and cooled at −40° C.) was added. Then, extraction with ether was conducted, and the extracted substance was dried with magnesium sulfate and concentrated. Thus, a crude product was obtained.

To the obtained crude product, methylene chloride (7 ml) and pyridine (0.7 ml) were added and ice-cooled. Then, acetic acid anhydride (1 ml, about 10 mmol) was added thereto and stirred at room temperature for 1 hour. 2 N hydrochloric acid was added thereto, and tetralin (1.08 ml, 8 mmol) as the internal standard was added and stirred. A sample of the reaction solution was taken out and measured by gas chromatography to calculate the yield of the generated product and the enantiomer excess (yield: 87%; 90% ee).

The invention claimed is:
1. A cyanation catalyst represented by formula (I):

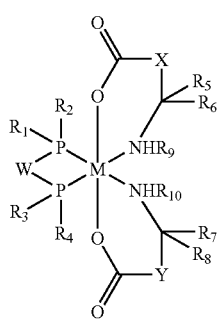

wherein $R_1$ through $R_4$ are the same as, or different from, one another, and are each an optionally substituted hydrocarbon group; $R_1$ and $R_2$ and/or $R_3$ and $R_4$ may form an optionally substituted carbon chain ring;
$R_5$ through $R_8$ are the same as, or different from, one another, and are each a hydrogen atom, or an optionally substituted hydrocarbon group; $R_5$ and $R_6$ and/or $R_7$ and $R_8$ may form an optionally substituted carbon chain ring;

$R_9$ and $R_{10}$ are the same as, or different from, each one other, and are each a hydrogen atom, or an optionally substituted hydrocarbon group;

W, X, and Y are the same as, or different from, one another, and are each an optionally substituted binding chain; or X and/or Y may be non-existent; and M is a metal or a metal ion.

2. The cyanation catalyst according to claim 1, wherein M is bivalent ruthenium.

3. The cyanation catalyst according to claim 1, wherein W is a 1,1'-binaphtyl group or a 1,1'-biphenyl group.

4. A cyanation catalyst made by reacting the cyanation catalyst according to claim 1 and a salt of a metal compound.

5. The cyanation catalyst according to claim 4, wherein the salt of the metal compound is at least one salt selected from the group consisting of lithium, sodium, potassium, cesium, magnesium, and lanthanoid, and an ammonium salt.

6. A method for producing the cyanation catalyst according to claim 1, the method comprising the steps of:

reacting a diphosphine represented by formula (A):

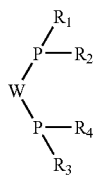
(A)

wherein $R_1$ through $R_4$ and W are the same as those in formula (I), with a metal complex comprising a metal or metal ion and;

reacting a reaction product obtained by the above step with an amino acid salt of formula (B) and/or an amino acid salt of formula (C) to produce a cyanation catalyst:

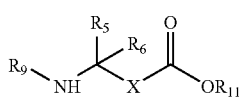
(B)

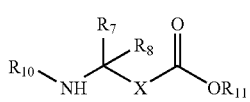
(C)

wherein X and $R_5$ through $R_{10}$ are the same as those in formula (I); and $R_{11}$ represents a hydrogen atom or a metal compound).

7. A method for producing a cyanation catalyst, comprising the step of reacting the cyanation catalyst of claim 6 with a salt of a metal compound.

8. A method for producing an optically active cyanohydrin of formula (F):

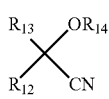
(F)

wherein $R_{12}$ is an optionally substituted group selected from an aromatic group, a hetero ring, a chain-like alkyl group, a cyclic alkyl group, an alkenyl group, and an alkynyl group; $R_{13}$ is a hydrogen atom, an optionally substituted alkyl group, or an optionally substituted aromatic group; wherein $R_{12}$ and $R_{13}$ may be bonded to each other to form a ring; and $R_{14}$ is a hydrogen atom, an optionally substituted hydrocarbon group, or an optionally substituted silyl group, the method comprising the steps of:

reacting, in the presence of a cyanation catalyst of claim 1, a carbonyl compound of formula (D) with a cyanide compound of formula (E):

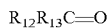 (D)

 (E)

wherein $R_{12}$ represents an aromatic group, a hetero ring, a chain-like alkyl group, a cyclic alkyl group, an alkenyl group or an alkynyl group, each of which may have a substituent; $R_{13}$ represents a hydrogen atom; or an alkyl group or an aromatic group, each of which may have a substituent; $R_{12}$ and $R_{13}$ may be bonded to each other to form a ring; and $R_{14}$ represents a hydrogen atom, an alkali metal, an optionally substituted hydrocarbon group, or an optionally substituted silyl group; and adding a salt of a metal compound to a reaction product obtained by the above step to cause a reaction to produce an optically active cyanohydrin.

9. A method for producing an optically active cyanohydrin of formula (F):

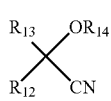
(F)

wherein $R_{12}$ represents an aromatic group, a hetero ring, a chain-like alkyl group, a cyclic alkyl group, an alkenyl group or an alkynyl group, each of which may have a substituent; $R_{13}$ represents a hydrogen atom; or an alkyl group or an aromatic group, each of which may have a substituent; $R_{12}$ and $R_{13}$ may be bonded to each other to form a ring; and $R_{14}$ represents a hydrogen atom, an optionally substituted hydrocarbon group, or an optionally substituted silyl group, the method comprising the step of:

reacting, in the presence of the cyanation catalyst according to claim 4, a carbonyl compound of formula (D) with a cyanide compound of formula (E) to produce an optically active cyanohydrin:

 (D)

 (E)

wherein $R_{12}$ represents an aromatic group, a hetero ring, a chain-like alkyl group, a cyclic alkyl group, an alkenyl group or an alkynyl group, each of which may have a substituent; $R_{13}$ represents a hydrogen atom; or an alkyl group or an aromatic group, each of which may have a substituent; and $R_{12}$ and $R_{13}$ may be bonded to each other to form a ring; and $R_{14}$ represents a hydrogen atom, an alkali metal, an optionally substituted hydrocarbon group, or an optionally substituted silyl group).

10. The method for producing a cyanohydrin according to claim 8, wherein $R_{14}$ is a hydrogen atom.

11. The method for producing a cyanohydrin according to claim 8, wherein $R_{14}$ is trimethylsilyl (TMS).

12. The method for producing a cyanohydrin according to claim 8, wherein an acid anhydride co-exists with the cyanohydrin.

13. The method for producing a cyanohydrin according to claim 9, wherein $R_{14}$ is a hydrogen atom.

14. The method for producing a cyanohydrin according to claim 9, wherein $R_{14}$ is trimethylsilyl (TMS).

15. The method for producing a cyanohydrin according to claim 9, wherein an acid anhydride co-exists with the cyanohydrin.

* * * * *